United States Patent [19]

Benedetti et al.

[11] Patent Number: 4,855,053

[45] Date of Patent: Aug. 8, 1989

[54] EXTRACTION OF ORGANIC COMPOUNDS FROM AQUEOUS SOLUTIONS

[75] Inventors: Charles Benedetti, Marseilles; Claude Gluntz, Cassis; Robert Pascal, Aubagne; Michel Stefanini, Plan De Cuques, all of France

[73] Assignee: Atochem, Puteaux, France

[21] Appl. No.: 944,271

[22] Filed: Dec. 18, 1986

[30] Foreign Application Priority Data

Dec. 18, 1985 [FR] France .................................. 85 18801

[51] Int. Cl.$^4$ ................................................. C02F 1/26
[52] U.S. Cl. ................................... 210/634; 210/908; 210/909; 562/554; 564/437; 564/497; 568/749; 568/755
[58] Field of Search ............... 210/634, 903, 908, 909; 203/43–46; 562/554; 564/437, 497; 568/749, 755; 570/211

[56] References Cited

U.S. PATENT DOCUMENTS

| | | | |
|---|---|---|---|
| 2,073,248 | 3/1937 | Mollinari | 210/634 |
| 2,199,786 | 5/1940 | Dierichs et al. | 568/749 |
| 4,582,937 | 4/1986 | Hiraga et al. | 564/497 |

FOREIGN PATENT DOCUMENTS 473680  9/1975  U.S.S.R. .............................. 210/634

*Primary Examiner*—Peter Hruskoci
*Attorney, Agent, or Firm*—Pennie & Edmonds

[57] ABSTRACT

Process for extracting organic compounds which are present in water in the form of solutions or suspensions by a liquid carboxylic acid which is immiscible with water. Branched or unbranched linear acids such as n-heptanoic, n-octanoic, or 2-ethylhexanoic acids make it possible to quantitatively extract compounds such as phenols, amines or amino acids from such aqueous solutions, thereby rendering the process useful for the purification of industrial wastewaters.

25 Claims, No Drawings

EXTRACTION OF ORGANIC COMPOUNDS FROM AQUEOUS SOLUTIONS

TECHNICAL FIELD

The invention relates to a process for the extraction of organic compounds contained in water in the form of solutions and/or suspensions. This process applies particularly to purification of wastewater containing such compounds and thus purification of wastewater containing such compounds and thus makes it possible to solve a particularly difficult problem.

BACKGROUND ART

It is difficult to purify wastewater from chemical or petrochemical plants before it can be discharged into the environment. The difficulty increases with the severity of the standards imposed by various laws intended to protect the environment, particularly those relating to the chemical oxygen demand (COD).

Numerous methods have been proposed to purify such waters; for example, those based on oxidation, passage over solid adsorbing substances (French Patent No. 84/15174), or centrifugation (French Patent No. 74/19446).

Liquid-liquid extraction has also been used; but the processes based on this principle require the use of costly, toxic chemicals which are applicable only to the removal of certain specific chemicals. For example, amine solutions have been proposed to extract humic acids (Vom Wasser -- 1973 -- 41-27-44), and 2-ethylhexanol has been used to purify wastewaters which result from the production of dialkylphthalates (Informations Chimie, No. 136, October 1974, pages 193-197). However, the solubility of these compounds in wastewater is, at times, significant, so that discharge of the purified waters becomes a separate problem, especially if the extracting compound remaining therein is not biodegradable.

The process that is the object of this invention utilizes a liquid-liquid extraction technique which does not exhibit the drawbacks indicated above.

SUMMARY OF THE INVENTION

This invention relates to a process for the extraction of organic compounds from aqueous solutions and/or suspensions of same, which comprises treating such solutions and/or suspensions with a liquid organic carboxylic acid that is immiscible with water at 20° C. in an amount sufficient to form an organic phase containing the organic compounds, and isolating the organic phase from the aqueous phase to extract the organic compounds from the solutions or suspensions. The organic acid has a solubility equal to or less than 5 grams per liter in water at 20° C., and preferably is n-heptanoic, n-octanoic, 2-ethylhexanoic, isopropyl acetic, or n-nonanoic acid or mixtures thereof.

Typical organic compounds to be extracted include amines, amino acids, lactams, phenol compounds, or mixtures thereof. Specific compounds to be extracted include heptylamine, N,N-dimethylbenzylamine, hexylamine, di-n-hexylamine, 11- aminoundecanoic acid, 12-aminoundecanoic acid, dodecanolactam, 2,3-dichlorophenol, ortho-chlorophenol, or mixtures thereof. The solution may be agitated to facilitate contact of the acid with the organic compound, wih a preferred treating step comprising a countercurrent extraction in a vertical column carried out at a temperature of between 25° and 60° C.

The process of the invention can also be used for reducing the amount of organic compounds from wastewater containing same, by treating the wastewater with a sufficient amount of a carboxylic acid which is immisicible with water and which is a liquid at the treatment temperature to form an organic phase containing the acid and a portion of the organic compounds, and separating the organic phase from the wastewater to reduce the content of the organic compounds by removal therefrom. The acid should be biodegradable so that any residual acid remaining in the wastewater can be discharged into the environment. The treating step may be repeated at least once to increase the amount of organic compound to be extracted.

DETAILED DESCRIPTION OF THE INVENTION

The present process first treats wastewater with a liquid organic carboxylic acid that is immiscible at the treatment temperature, which results in the formation of two separate phases, one organic and the other aqueous. Then, these two phases are separated to remove the organics from the wastewater.

The compounds initially contained in the wastewater are distributed, according to a certain partition coefficient, between these two phases. If necessary, it is possible to repeat the extraction several times for best results. The compounds dissolved in the organic phase are separated and recovered by any suitable method. Distillation, for example, can be used if they are volatile.

The preferred carboxylic acids are immiscible in water; in other words, they are insoluble or only slightly soluble in water. Most preferably, an acid will be used whose solubility in water is at most equal to 5 grams per liter at 20° C. This acid can be aliphatic, linear or branched, saturated or unsaturated, cyclic, or heterocyclic; it can also contain heteroatoms such as sulfur, phosphorus, or nitrogen. Of course, it is also possible to use a mixture of acids in the invention. N-heptanoic, 2-ethylhexanoic, isopropyl acetic, n-nonanoic, called pelargonic, acids or mixtures thereof are particularly well suited with n-heptanoic acid being especially advantageous because it is easily biodegradable.

The following compounds contained in the wastewater to be treated can be extracted quantitatively with the acid or acid mixture: amines, amino acids, lactams and, surprisingly, phenols. If the compound to be extracted is only slightly soluble in water and is present in an amount which exceeds this solubility, both a solution and a suspension will be present, and either can be treated by the processes of theis invention.

The usual liquid-liquid extraction methods are used to perform this extraction; for example, after the acid has been put in aqueous suspension or solution, held in a container, the whole can be subjected to a vigorous agitation to disperse the acid in the form of droplets then to allow it to decant; it is also possible to perform a countercurrent extraction in a vertical column.

The extraction can be performed at any temperature; previous routine laboratory tests will make it possible to determine the optimal temperature for each particular case.

EXAMPLES

In the following examples, given by way of illustration and without the slightest limiting character, the aqueous solutions or suspensions were prepared by adding to a liter of water, with moderate agitation, 1 to 2 percent (or from 10 to 20 grams) of the organic compound studied, this water being contained in a reactor provided with a double jacket, passed through by a heat transfer medium, making it possible to maintain a given temperature.

Then carboxylic acid is introduced at a rate of 2 or 4.6 parts by weight percent of water—after 10 minutes of agitation followed by decanting, the two phases, i.e., the supernatant organic phase and aqueous phase, are separated, weighed and the amount of unextracted organic compound determined by analysis in the aqueous phase—either by evaporation (determination of the dry extract) or by potentiometric metering with hydrochloric acid in the case of amino compounds.

If we designate:

Q, the mass of the organic compound to be extracted that is used,

X, its content in percent, by weight, in the aqueous phase after extraction,

Y, its content in percent, by weight, in the organic phase after extraction,

M, the mass of the aqueous phase after extraction, m, the mass of the organic phase after extraction, $K_d$, the partition coefficient of the organic compound between the organic phase and the aqueous phase, after extraction, and $R_d$, the extraction yield of the compound, in percent, we will have:

$$Q = Y(m/100) + X(M/100)$$

or:

$$Y = (Q - X(M/100))(100/m)$$

with $$K_d = Y/X$$

and $$R_d \text{ (in percent)} = (Y)(m/Q)$$

Table No. I shows the results of extraction tests performed at a temperature of 60° with n-heptanoic acid on various organic compounds in an aqueous solution.

Table No. II shows the extraction results performed at:

two different temperatures: 25° and 60° C.

on aqueous compositions whose initial composition at 25° C. was 20 grams of 11-aminoundecanoic acid per 1 liter of water, by means of various acids of which EMERY acid 12-10 of the EMERY company (a mixture of hexanoic and octanoic acids) at a rate of 5% by volume in relation to the water used or 50 cc, all these acids having a solubility in water of less than 5 grams per liter at 20° C.

TABLE II

| Nature of acid | 25° C. | | 60° C. | |
| --- | --- | --- | --- | --- |
|  | Kd | Rd | Kd | Rd |
| n-heptanoic | 76.8 | 81.7 | 52.8 | 77.3 |
| n-octanoic | 187.7 | 92.9 | 124.8 | 89.2 |
| 2-ethylhexanoic | 288 | 95.1 | 91.3 | 84.7 |
| n-nonanoic | 156.1 | 91.2 | 46.7 | 73.2 |
| Emery 12-10 | 87.5 | 84.2 | 56.3 | 77.4 |

Table No. III illustrates a comparison of the extractive power of n-heptanoic and n-octanoic acids at 60° C. on two different compounds: dodecanolactam and 2,3-dichlorophenol.

TABLE III

| | Nature of extract compound | | | |
| --- | --- | --- | --- | --- |
| | Dodecanolactam | | 2,3-Dichlorophenol | |
| Nature of acid | Kd | Rd | Kd | Rd |
| n-heptanoic | 302 | 95.2 | 299 | 94.5 |
| n-octanoic | 344 | 95.7 | 22200 | 99.9 |

While it is apparent that the invention herein disclosed is well calculated to fulfill the objects above stated, it will be appreciated that numerous modifications and embodiments may be devised by those skilled in the art, and it is intended that the appended claims over all such modifications and embodiments as fall within the true spirit and scope of the present invention.

TABLE I

| Nature of compound to be extracted | COMPOSITIONS OF THE INITIAL AQUEOUS SOLUTION OR SUSPENSION | | RESULTS AFTER EXTRACTION | | | |
| --- | --- | --- | --- | --- | --- | --- |
| | Compound content in % | Acid content in % | X in % | Y in % | Partition coefficient Kd | Yield Rd in % |
| Phenol | 1 | 2 | 0.5 | 20 | 33 | 50 |
| 2,3-Dichlorophenol | 2 | 4.6 | 0.118 | 32 | 299 | 94.5 |
| Ortho-chlorophenol | 2 | 4.6 | 0.0019 | 99.91 | 21910 | 99.9 |
| Diethylamine | 2 | 4.6 | 1.7 | 22.4 | 13 | 12.5 |
| Triethylamine | 1 | 2 | 0.85 | 29.4 | 35 | 15 |
| Heptylamine | 1 | 2 | 0.35 | 27.5 | 79 | 65 |
| N,N—Dimethylbenzylamine | 2 | 4.6 | 0.16 | 40.8 | 252 | 91.9 |
| Hexylamine | 2 | 4.6 | 0.135 | 31.1 | 230 | 93.3 |
| Di-n-hexylamine | 2 | 4.6 | 0.003 | 91.5 | 10500 | 99.9 |
| 11-Aminoundecanoic acid | 2 | 4.6 | 0.48 | 25.36 | 52.83 | 77.35 |
| 12-Aminododecanoic acid | 1 | 2 | 0.3 | 25.9 | 86 | 70 |
| Dodecanolactam | 2 | 4.6 | 0.1 | 30.22 | 302 | 95.2 |

What is claimed is:

1. A process for the extraction of organic compounds comprising an amino acid, a lactam, a phenol compound or mixtures thereof from aqueous solutions and/or suspensions of same, which consists essentially of:

treating said solutions and/or suspensions with a liquid organic carboxylic acid that is immiscible with water at 20° C. in an amount sufficient to form an organic phase, containing the organic compounds, and isolating the organic phase from the aqueous phase to extract said organic compounds from said solutions or suspensions.

2. The process according to claim 1, wherein the organic acid has a solubility equal to or less than 5 grams per liter in water at 20° C.

3. The process according to claim 2, wherein the acid comprises n-heptanoic, n-octanoic, 2-ethylhexanoic, isopropyl acetic, n-nonanoic acid or mixtures thereof.

4. The process of claim1 wherein the solution is agitated to facilitate contact of the acid with the organic compound.

5. The process of claim 1 wherein the treating step comprises a countercurrent extraction in a vertical column.

6. The process according to claim 1 wherein the extraction is carried out at a temperature of between 25° and 60° C.

7. The method of claim 1 wherein the amino acid is 11-aminoundecanoic acid or 12-aminododecanoic acid, the lactam is dodecanolactam, and the phenol compound is 2,3-dichlorophenol or orthochorophenol.

8. A process for the extraction of organic compounds comprising, amino acids, lactams, or phenols from an aqueous solution containing same which consists essentially of treating said solution with a sufficient amount of n-heptanoic, n-octanoic, 2-ethyl hexanoic, isopropyl acetic or n-nonanoic acid or mixtures therein to form an organic phase containing the organic compound and the acid, and separating the organic phase from the aqueous solution to extract said organic compounds from said solution.

9. The process according to claim 8 which further comprises recovering the organic compounds from the organic phase.

10. The process according to claim 8 wherein the extraction is carried out at a temperature of between 25° and 60° C.

11. The process according to claim 8 wherein the treating step is repeated at least once to increase the amount of organic compound to be extracted.

12. The method of claim 8 wherein the amino acid is 11-aminoundecanoic acid or 12-aminododecanoic acid, the lactam is dodecanolactam, and the phenol compound is 2,3-dichlorophenol or orthochorophenol.

13. A process for reducing the amount of organic compounds comprising heptylamine, N,N-dimethyl benzylamine, hexylamine, di-N-hexylamine, an amino acid, a lactam, a phenol compound, or mixtures thereof from wastewater containing same, which consists essentially of treating the wastewater with a sufficient amount of a carboxylic acid which is immisicible with water and which is a liquid at the treatment temperature to form an organic phase containing the acid and a portion of the organic compounds, and separating the organic phase from the wastewater to reduce the content of said organic compounds by removal therefrom.

14. The process of claim 13 wherein the solution is agitated to facilitate contact of the acid with the organic compound.

15. The process of claim 13 wherein the acid is biodegradable so that any residual acid remaining in the wastewater can be discharged into the environment.

16. The process of claim 13 wherein the treating step comprises a countercurrent extraction in a vertical column.

17. The process according to claim 13 wherein the extraction is carried out at a temperature of between 25° and 60° C.

18. The process according claim 13 wherein the treating step is repeated at least once to increase the amount of organic compound to be extracted.

19. The process according to claim 13 wherein the acid comprises n-heptanoic, n-octanoic, 2-ethylhexanoic, isopropyl acetic, n-nonanoic acid or mixtures thereof.

20. The method of claim 13 wherein the amino acid is 11-aminoundecanoic acid or 12-aminododecanoic acid, the lactam is dodecanolactam, and the phenol compound is 2,3-dichlorophenol or orthochorophenol.

21. A process for the extraction of organic compounds of heptylamine, N,N-dimethylbenzylamine, hexylamine, di-n-hexylamine, 11-aminoundecanoic acid, 12-aminododecanoic acid, dodecanolactam, 2,3-dichlorophenol, ortho-chlorophenol or mixtures thereof from aqueous solutions and/or suspensions of same, which consists essentially of:

treating said solutions and/or suspensions with a liquid organic carboxylic acid that is immiscible with water at 20° C. in an amount sufficient to form an organic phase containing the organic compounds; and isolating the organic phase from the aqueous phase to extract said organic compounds from said solutions or suspension.

22. The process of claim 21, wherein the organic acid has a solubility equal to or less than 5 grams per liter in water at 20° C.

23. The process of claim 21, wherein the acid is n-heptanoic, n-octanoic, 2-ethylhexanoic, ispropyl acetic, n-nonanoic acid or mixtures thereof.

24. The process of claim 21 wherein the solution is agitated to facilitate contact of the acid with the organic compound.

25. The process of claim 21 wherein the treating step comprises a countercurrent extraction in a vertical column, wherein the extraction is carried out at a temperature of between 25° and 60° C.

* * * * *